US010662466B2

(12) United States Patent
Berry et al.

(10) Patent No.: US 10,662,466 B2
(45) Date of Patent: May 26, 2020

(54) MAGNETIC BASE FOR COLLECTION AND RELEASE OF PARAMAGNETIC PARTICLES

(71) Applicant: Salus Discovery, LLC, Monona, WI (US)

(72) Inventors: Scott Berry, Madison, WI (US); David J. Guckenberger, Madison, WI (US)

(73) Assignee: SALUS DISCOVERY, LLC, Monona, WI (US)

( * ) Notice: Subject to any disclaimer, the term of this patent is extended or adjusted under 35 U.S.C. 154(b) by 151 days.

(21) Appl. No.: 15/873,526

(22) Filed: Jan. 17, 2018

(65) Prior Publication Data

US 2018/0201984 A1 Jul. 19, 2018

Related U.S. Application Data

(60) Provisional application No. 62/447,686, filed on Jan. 18, 2017.

(51) Int. Cl.
| | |
|---|---|
| *C12Q 1/68* | (2018.01) |
| *C12N 15/10* | (2006.01) |
| *G01N 35/02* | (2006.01) |
| *G01N 35/10* | (2006.01) |
| *B01L 9/06* | (2006.01) |
| *G01N 35/00* | (2006.01) |
| *C12Q 1/6834* | (2018.01) |
| *C12Q 1/6832* | (2018.01) |
| *C12Q 1/6806* | (2018.01) |

(52) U.S. Cl.
CPC .............. *C12Q 1/6834* (2013.01); *B01L 9/06* (2013.01); *C12N 15/1003* (2013.01); *C12Q 1/6806* (2013.01); *C12Q 1/6832* (2013.01); *G01N 35/0098* (2013.01); *G01N 35/0099* (2013.01); *G01N 35/025* (2013.01); *G01N 35/1065* (2013.01)

(58) Field of Classification Search
CPC .. C12Q 1/6834; C12Q 1/6806; C12Q 1/6832; G01N 35/0098; G01N 35/0099; G01N 35/025; G01N 35/1065; G01N 35/026; G01N 35/10; G01N 35/1009; G01N 35/107; G01N 1/40; G01N 2001/4038; G01N 2035/00564; C12N 15/1003; B01L 9/06; B01L 3/502; B01L 3/5025; B01L 3/5027; B01L 3/502707; B01L 3/50273; B01L 3/502746; B01L 9/52; B01L 9/523; B01L 9/54; B01L 2300/06; B01L 2300/0609; B01L 2300/0829; B01L 2300/0861; B01L 2300/0867; B03C 1/04; B03C 1/06; B03C 2201/18
USPC ......... 422/63, 551, 552, 559, 560, 501, 509; 436/43, 46, 47, 50, 174
See application file for complete search history.

(56) References Cited

U.S. PATENT DOCUMENTS 3,938,961 A * 2/1976 Lanier .................. B01L 3/5085
422/552
4,986,965 A * 1/1991 Ushikubo ............... B01L 3/508
220/737

(Continued)

*Primary Examiner* — Joseph W Drodge
(74) *Attorney, Agent, or Firm* — Casimir Jones, S.C.; Tanya Arenson (57) ABSTRACT

Provided herein are devices, systems, and methods for magnetic purification of sample components. In particular, provided herein are device bases, systems, and methods for manipulating magnetic particles.

18 Claims, 8 Drawing Sheets

(56) References Cited

U.S. PATENT DOCUMENTS

| | | | |
|---|---|---|---|
| 6,448,092 B1* | 9/2002 | Tuunanen | B03C 1/284 |
| | | | 436/526 |
| 6,461,034 B1* | 10/2002 | Cleveland | B01F 7/00291 |
| | | | 366/273 |
| 8,603,416 B2* | 12/2013 | Beebe | C07K 1/22 |
| | | | 422/501 |
| 10,337,967 B2* | 7/2019 | Guckenberger | G01N 1/40 |
| 2004/0022677 A1* | 2/2004 | Wohlstadter | B01L 9/50 |
| | | | 422/52 |
| 2007/0031296 A1* | 2/2007 | Coulling | B01L 3/50855 |
| | | | 422/400 |
| 2007/0148785 A1* | 6/2007 | Lutze | B03C 1/286 |
| | | | 436/526 |
| 2009/0117004 A1* | 5/2009 | Fritchie | B01L 3/0289 |
| | | | 422/63 |
| 2011/0306097 A1* | 12/2011 | Belz | B01L 3/50853 |
| | | | 435/91.21 |
| 2014/0065622 A1* | 3/2014 | Beebe | B01L 3/502761 |
| | | | 435/6.12 |
| 2014/0190894 A1* | 7/2014 | Beebe | G01N 1/34 |
| | | | 210/695 |

* cited by examiner

MAGNETIC BASE FOR COLLECTION AND RELEASE OF PARAMAGNETIC PARTICLES

This application claims priority to provisional patent application 62/447,686, filed Jan. 18, 2017, which is herein incorporated by reference in its entirety.

FIELD

Provided herein are devices, systems, and methods for magnetic purification of sample components. In particular, provided herein are device bases, systems, and methods for manipulating magnetic particles.

BACKGROUND

Processing of liquid samples to isolate desired components from other components that may be present in the liquid samples is ubiquitous in a variety of fields. For example, DNA sequencing can involve first lysing cells containing the target DNA to form a lysate, a complex mixture of the desired nucleic acids and other components such as cellular debris and lysing reagents. Before the desired nucleic acids can be amplified, detected and quantified, they often must be isolated from these other components.

SUMMARY

Provided herein are devices, systems, and methods for magnetic purification of sample components. In particular, provided herein are device bases, systems, and methods for manipulating magnetic particles.

For example, in some embodiments, provided herein is a magnetic box for a sample plate of a sample processing system, the magnetic box comprising: a) a top surface comprising a reagent plate mounting component; b) a bottom surface comprising a magnet management component, wherein the top surface and said bottom surface define a magnet mounting cavity; and c) a lower magnet disposed in the magnet mounting cavity. In some embodiments, the magnet management component comprises a plurality of ridges (e.g., sawtooth shaped ridges) on the bottom of the top surface. In some embodiments, the ridges have a depth of at least half the length or thickness of the lower magnet. In some embodiments, the ridges are on a replaceable strip. In some embodiments, the replaceable strip is integrated into a lid of the box or is freestanding. In some embodiments, the ridges comprise one or more ramped edges. In some embodiments, the ridges comprise a pocket. In some embodiments, the ridges comprise one or more square edges. In some embodiments, the box further comprises a ramp on the bottom surface.

In some embodiments, the magnet management component comprises a plurality of adhesive and/or magnetic or paramagnetic plates disposed on the bottom of the top surface. In some embodiments, the plates are composed of iron or a ferrous metal. The present disclosure is not limited to a particular material for the magnetic box. Examples include, but are not limited to, a transparent plastic, a translucent plastic, ceramic, or a non-metallic metal. In some embodiments, the box further comprises a base and/or lid.

Further embodiments provide a system, comprising: a) the magnetic boxes described herein; and b) a magnetic head comprising a top magnet. In some embodiments, the system further comprises one or more additional components selected from, for example, a sample handling plate comprising a plurality of sample compartments, magnetic or paramagnetic particles (PMP) (e.g., beads), a drive system configured to move said magnetic head, a sample handling plate cover, or a control component. In some embodiments, the ridges are vertically oriented with wells of the sample handling plate. In some embodiments, the ridges are not vertically oriented with wells of the sample handling plate. In some embodiments, the metal plates are vertically oriented with a subset of sample handling compartment of the sample handling plate. In some embodiments, the sample handling plate is a multi-well plate. In some embodiments, the sample handling plate is not in fluid communication with the magnetic base. In some embodiments, the top magnet and the lower magnet are in magnetic communication with the sample handling plate. In some embodiments, the top magnet is configured to be in a upper or lower vertical position in the magnetic head.

Additional embodiments provide a method of processing a sample, comprising one or more (e.g., all) of: a) contacting a sample and a plurality of magnetic beads with a first sample compartment of the system described herein; b) moving the top magnet to a second sample compartment under conditions such that the lower magnet is vertically aligned with the top magnet and wherein the magnetic management component secures the lower magnet in the second sample compartment; c) returning the top magnet to said first sample compartment; d) lowering the top magnet such that the magnetic beads are magnetically contacted with the top magnet; and e) moving the top magnet and the magnetic beads to the second sample compartment. In some embodiments, the method further comprises the step f) of removing the magnetic head from magnetic communication with the magnetic beads and the lower magnet such that the magnetic beads are free floating in the second sample compartment. In some embodiments, the method further comprises the step of resetting the lower magnet to said first sample compartment. In some embodiments, the sample or a component thereof is attached to the magnetic particles (e.g., beads). In some embodiments, the sample is a blood sample, a urine sample, a sputum sample, a semen sample, a cellular sample, an environmental sample, or a microorganism. In some embodiments, the method comprises isolating or analyzing an analyte (e.g., a nucleic acid, protein, metabolite, etc.). In some embodiments, the method further employs a hybridization assay, a sequencing assay, an amplification assay, or an immunoassay on a sample isolated using the systems and methods described herein.

Additional embodiments are described herein.

BRIEF DESCRIPTION OF THE DRAWINGS

FIG. 5A-E show exemplary methods of using the devices described herein.

FIG. 6A-B show exemplary magnet configurations.

DEFINITIONS

To facilitate an understanding of the present disclosure, a number of terms and phrases are defined below:

The term "sample" is used in its broadest sense. On the one hand it is meant to include a specimen or culture. On the other hand, it is meant to include both biological and environmental samples. A sample may include a specimen of synthetic origin.

As used herein, the term "cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo.

DETAILED DESCRIPTION

Provided herein are devices, systems, and methods for magnetic purification of sample components. In particular, provided herein are device bases, systems, and methods for manipulating magnetic particles.

Figure 1:
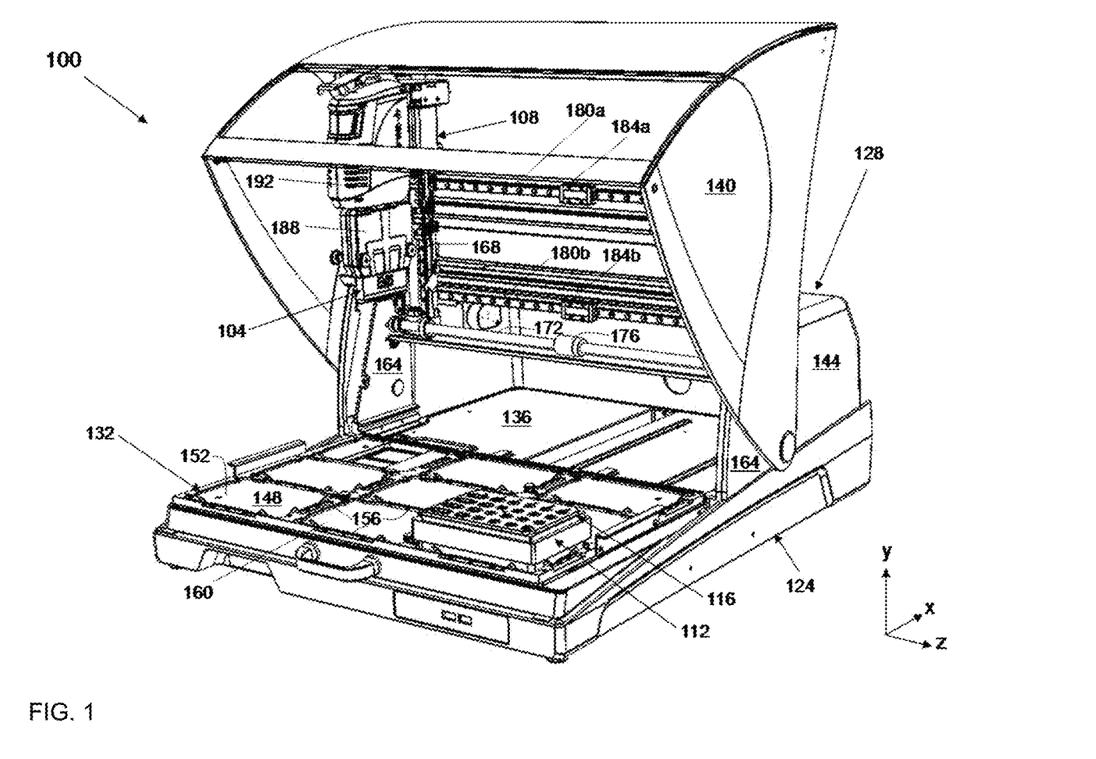
FIG. 1 depicts a perspective view of an exemplary sample processing system in accordance with an illustrative embodiment.

For example, in some embodiments, provided herein is a magnetic box (e.g., for use in a magnetic sample handling apparatus). The magnetic boxes described herein provide improved control over collection and deposition of magnetic particles relative to existing sample handling systems. In some embodiments, the magnetic boxes described herein are provided in a well plate holder having a free-moving magnet within (e.g., in a system similar to that described in FIG. 1). The exemplary system 100 in FIG. 1 comprises a magnetic head 104, a drive system 108, a magnetic base 112, and a sample handling plate 116. Sample processing system 100 may also include a support assembly configured to support and enclose various components of sample processing system 100. By way of illustration, the support assembly may include a base 124, a cover 128, and a work bed 132.

In prior systems, this magnet, which tracks an automation-driven magnet above, is used to pull magnetic beads containing biological analytes into the plate. This action serves to purify the analyte. A current limitation of such systems is that the lower magnet (responsible for depositing biological analyte-laden magnetic beads into a well plate to achieve purification) is magnetically linked with the "head" magnetic assembly positioned above the magnetic box. This means that both magnets have the same positioning in the X-Y plane (e.g., the lower magnet "follows" the position of the head magnet). Since the magnetic beads are positioned between these two magnets, magnetic manipulation of the beads (typically paramagnetic in nature) is limited as each magnet exerts an opposing pull on the beads. Previously, this was compensated for by raising and lowering the upper "head" magnet.

Provided herein are devices, systems, and methods that allow for the de-coupling of the head and lower (e.g., box) magnets' positions, creating more robust and faster operation.

For example, in some embodiments, provided herein are magnetic boxes comprising a magnet management component that allows independent placement and securing of a lower box magnet. The present disclosure is not limited to particular magnet management components. Examples include, but are not limited to, ridges (e.g., sawtooth shaped ridges) forming grooves there between on the underside of the box and magnetic or paramagnetic plates on the underside of the upper surface of the box. In some embodiments, the magnet management component physically (e.g., with ridges) secures the magnet independent of the position of the upper or top magnet. In some embodiments, metal plates are provided with the magnet management component to secure the magnet in a desired position independent of the upper or top magnet.

Figure 2:
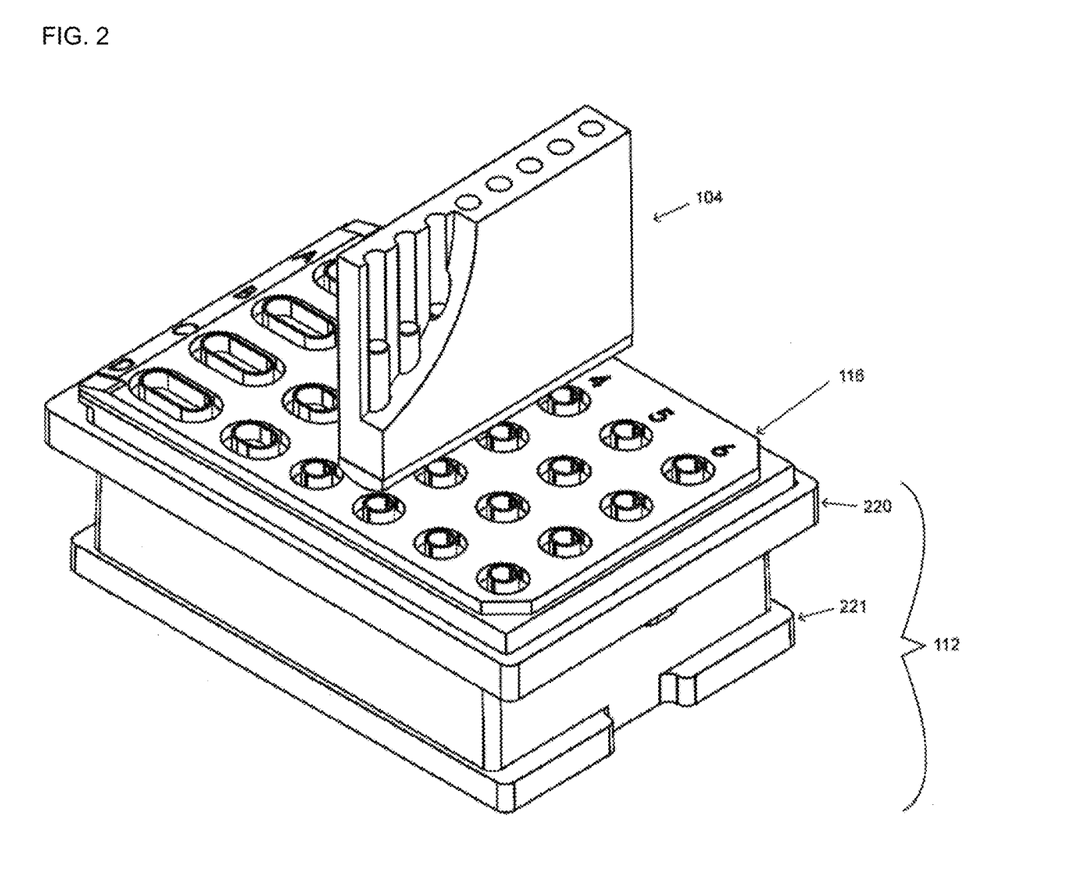
FIG. 2 shows a schematic or an exemplary sample purification device with magnetic head, plat and magnetic box.
Figure 3:
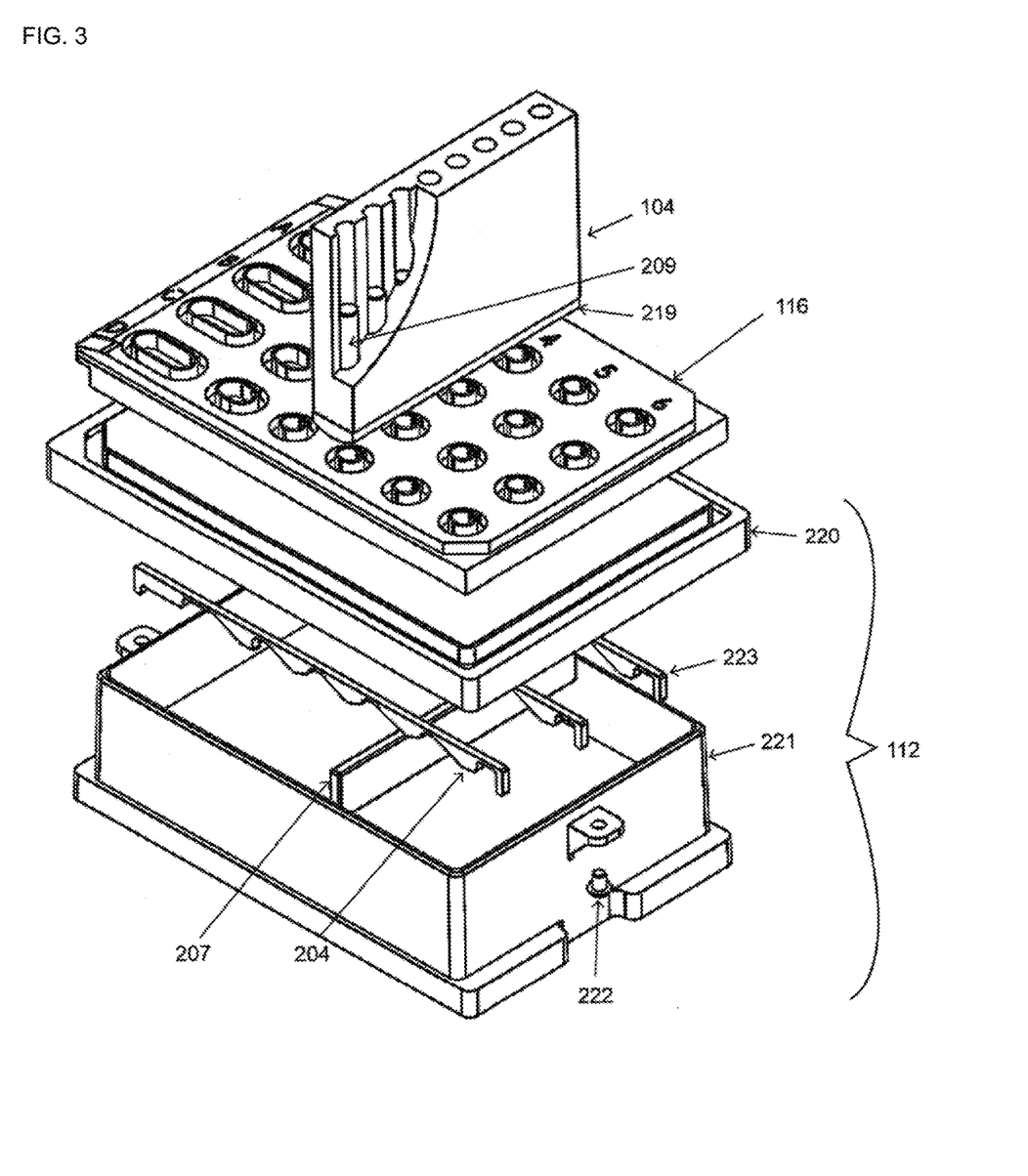
FIG. 3 shows a close up view of FIG. 2.
Figure 4:
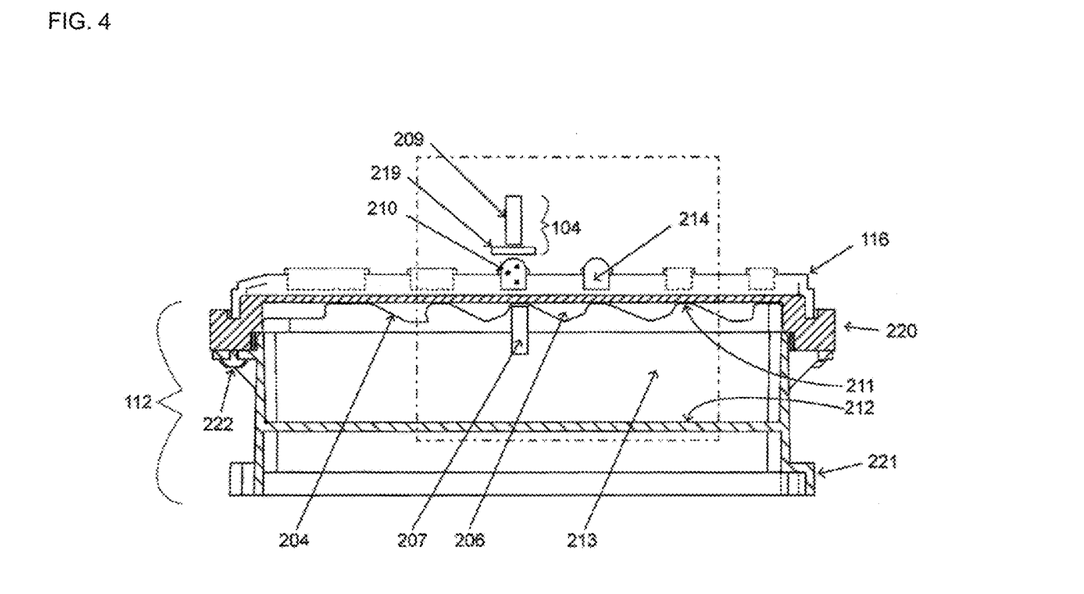
FIG. 4 shows a cross section view of FIG. 2.

Exemplary magnetic devices (e.g., boxes) are shown in FIGS. 2-4. FIG. 2 shows a schematic of an exemplary magnetic device or box. The magnetic device comprises magnetic head 104, plate 116, and magnetic box 112. The magnetic box 112 further comprises lid 220 and base 221. The present disclosure is not limited to a particular material for the magnetic device, box or components thereof. Examples include, but are not limited to, a transparent plastic, a translucent plastic, ceramic, or a non-metallic metal. Any number of suitable rigid plastics or polymers are suitable (e.g., polystyrene).

FIG. 3 shows an expanded view of FIG. 2. FIG. 3 shows magnetic head 104, top magnet 209, and barrier strip 219. Also shown is plate 116, box 112, lid 220, base 221, and fastener 222. FIG. 3 further show sawtooth ridges or teeth 204 integrated into replaceable strip 223. In the embodiment shown in FIG. 3 teeth 204 are on detachable strip 223. The strip 223 can be integrated into lid 220 or are a stand-alone feature. In some embodiments (not shown in FIG. 3), sawtooth ridges or teeth 204 are fastened directly to lid 220.

FIG. 4 shows a cross-section view of FIG. 2. Dashed line represents the view field used for subsequent figures. Shown is magnetic head 104, top magnet 209, barrier strip 219, beads 210, sample compartments 214, plate 116, magnetic box 112, fastener 222, lid 220, base 221, upper surface 211, lower surface 212, sawtooth ridges or teeth 204, lower magnet 207 and a magnetic mounting cavity 213. The sawtooth shaped ridges 204 comprise a vertical distance 206.

The present disclosure is not limited to a particular material for the magnetic device, box or components thereof. Examples include, but are not limited to, a transparent plastic, a translucent plastic, ceramic, or a non-metallic metal. Any number of suitable rigid plastics or polymers are suitable (e.g., polystyrene).

In some embodiments, magnetic box 112 is provided as part of a sample handling device or system 100 comprising a sample handling (e.g., reagent) plate 116 and magnetic head 104 comprising top magnet 209. In some embodiments, the sample handling plate 116 comprises a plurality of sample compartments (e.g., wells) 214. In some embodiments, the sample handling plate 116 is a multiwell plate. In some embodiments, the magnetic base is fluidly isolated from the sample handling plate.

In some embodiments, systems comprise magnetic particles (e.g., beads) 210. In some embodiments, the magnetic beads are configured to bind sample or analyte (e.g., with an affinity capture moiety). A variety of sample analysis beads are commercially available and suitable for use in the systems described herein.

Figure 5A:
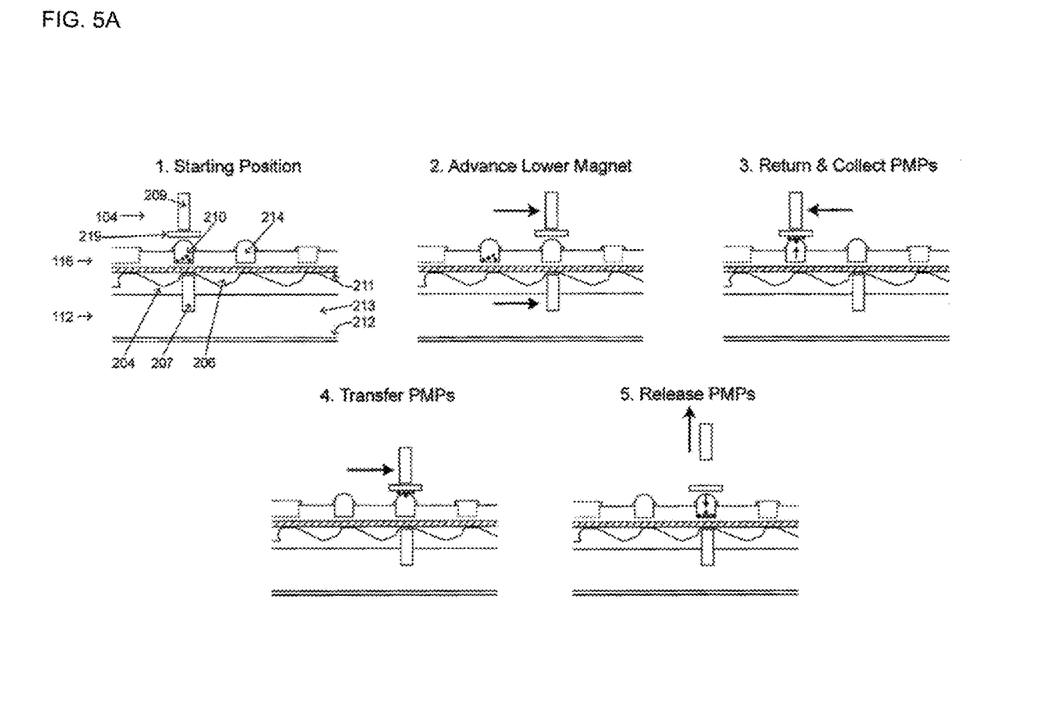
FIG. 5A shows an exemplary device in use with sawtooth shaped ridges.

FIGS. 5A-E show methods of using the described magnetic bases to process samples. FIG. 5A shows the system in use. The teeth 204 have a notched region to hold the magnet in place. In some embodiments, as shown in FIG. 5A, the teeth 204 has a double ramp facing both directions as shown by vertical distance 206. A sample (e.g., cell, microorganism, tissue, blood, sputum, urine, or other bodily fluid) is placed with magnetic beads in a first sample compartment 214. The top magnet is placed in its upper position and is aligned with the lower magnet. Because the top magnet is in an upper position, the magnetic beads are not in magnetic contact with either the top or lower magnet and are free floating. In the next step, the magnetic head 104 is used to move lower magnet to a second (e.g., adjacent) compartment of the sample handling plate (top middle panel of FIG. 5A). The head 104 is used to move the top magnet back to the first compartment. The top magnet is placed in its lower position such that the magnetic beads attach to the top magnet (top right panel of FIG. 5A). The magnet management system is used to secure the lower magnet below the second sample handling plate when the top magnet is moved. For example, either the sawtooth shaped ridges prevent the lower magnet from moving or the metal plate is used to secure the lower magnet. The top magnet is then used to move the magnetic beads to the second sample compartment (lower left panel). In some embodiments, the magnetic head 104 is raised at this point (lower right panel of FIG. 5A). In some embodiments, the lower magnet is then reset to its original position below the first sample handling compartment. In some embodiments, the above steps are repeated one or more times in order to complete all sample handling steps. In some embodiments, magnetic bases comprise a plurality of magnet management components in parallel for multiplexing.

Figure 5B:
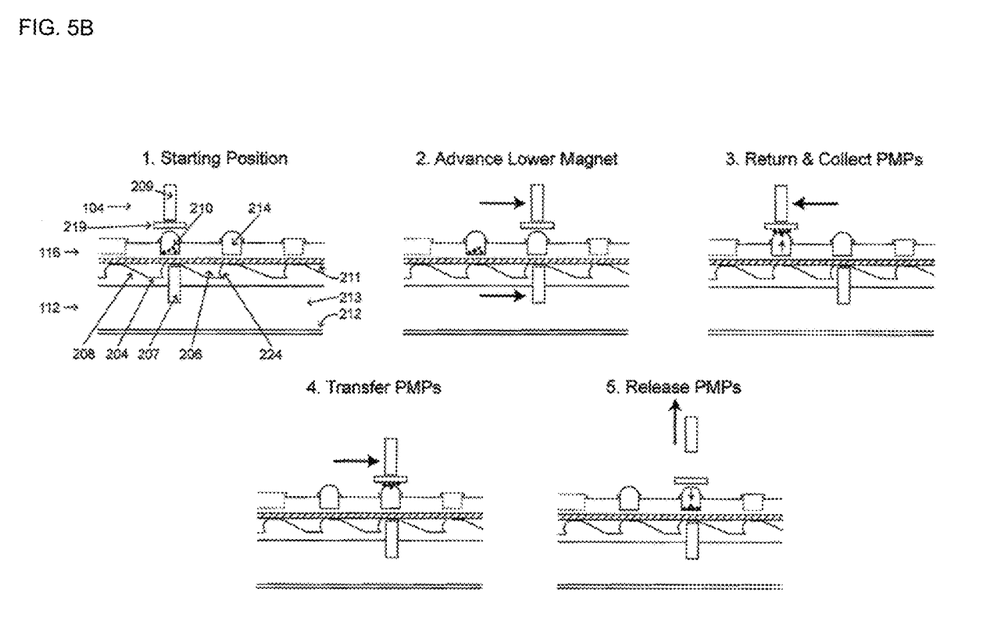
FIG. 5B shows an exemplary device in use with ramped edges on the sawtooth shaped ridges and a pocket in the sawtooth shaped ridges.

FIG. 5B shows a magnetic system in use. The operation is the same as described in FIG. 5A. FIG. 5B shows further embodiments with ramped edge 208 and pocket in tooth 224. In some embodiments, ramp 208 is used to help the magnet move smoothly. In some embodiments, pocket 224 serves to help hold the magnet in place. Pocket 224 is particularly beneficial if magnets are heavy (prevents magnet from falling) and beneficial for magnets that are wider than they are long (e.g., FIG. 6A).

Figure 5C:
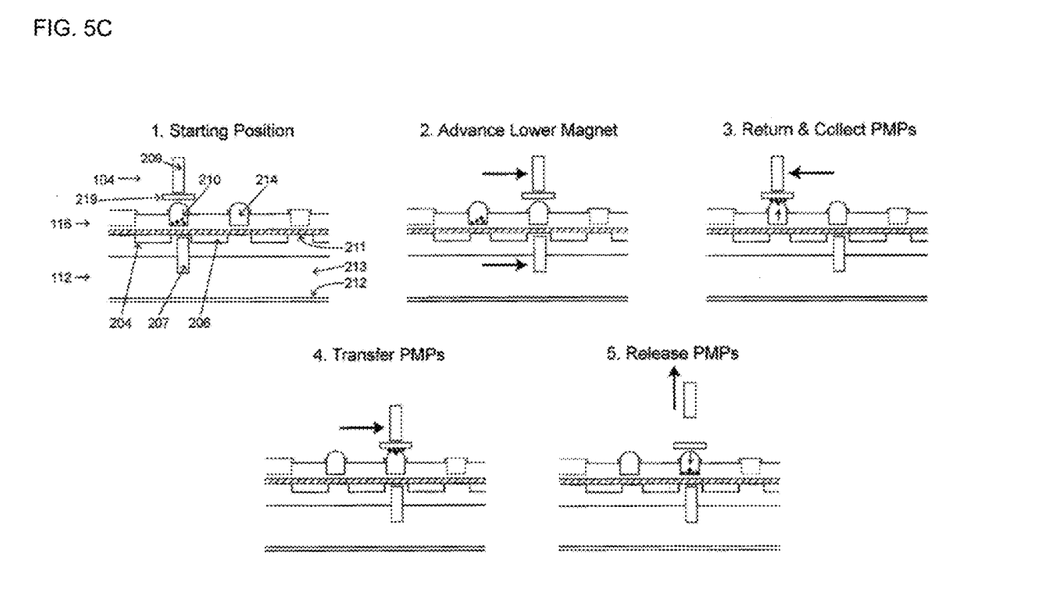
FIG. 5C shows an exemplary device in use where the sawtooth ridges was flat or square edges.

FIG. 5C shows a further embodiment of a magnetic system in use. The operation is the same as described in FIG. 5A. In the embodiment shown in FIG. 5C, teeth 204 have flat/square edges instead of ramped edges. In some embodiments, the square edge is the leading or lagging edge.

Figure 5D:
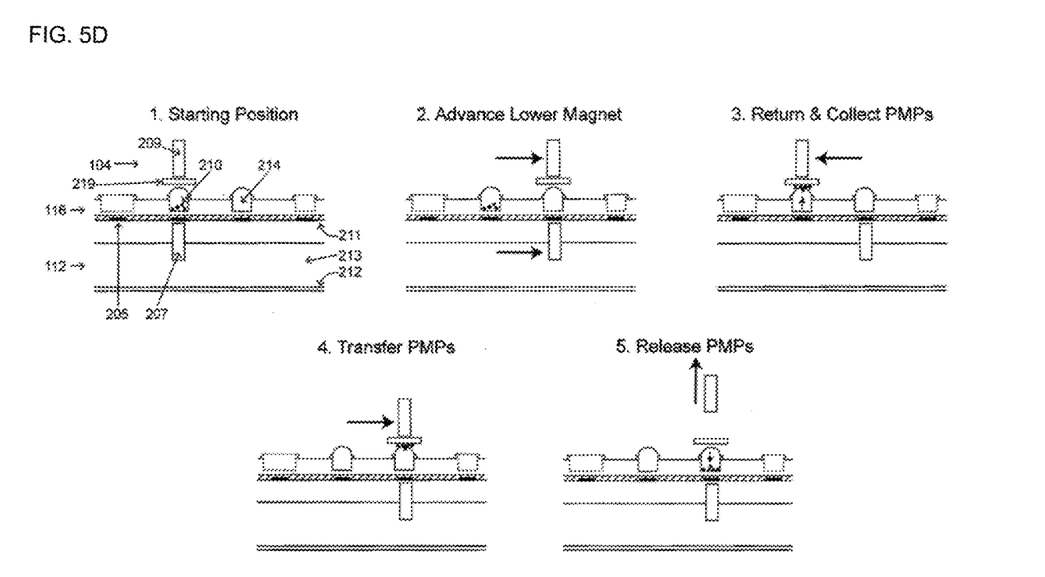
FIG. 5D shows an exemplary device in use comprising adhesive material.

FIG. 5D shows a further embodiment of a magnetic system in use. The operation is the same as described in FIG. 5A. In the embodiment shown in FIG. 5D, the teeth 204 are replaced with attachment zone 205. In some embodiments, the attachment zone comprises magnetic material and/or adhesive material that serves to hold the magnet in place. In some embodiments, the attachment zone 205 is a metal plate comprising a magnetic or paramagnetic material.

Figure 5E:
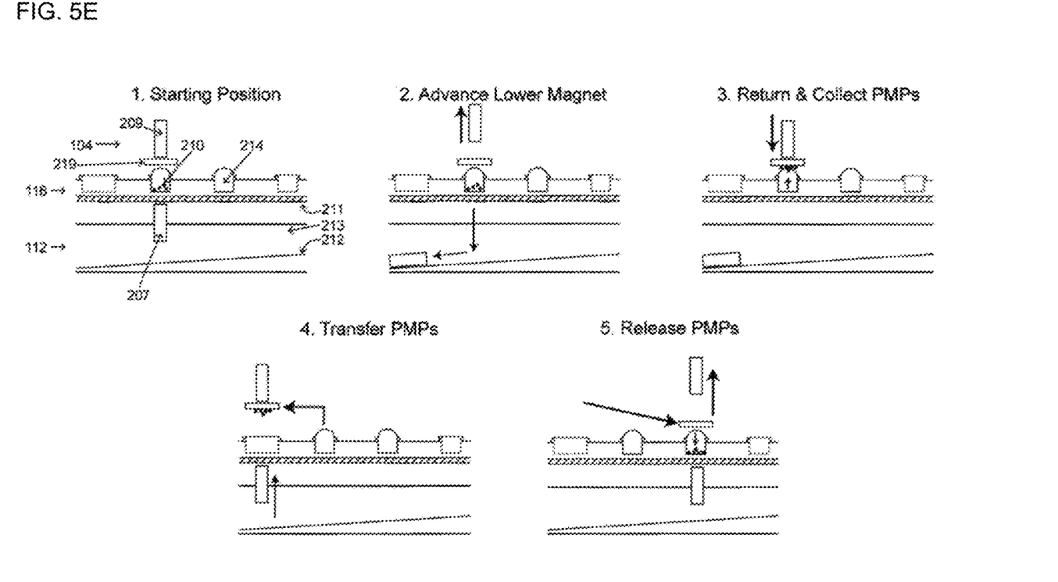
FIG. 5E shows an exemplary device in use comprising a ramp and sloped bottom surface.

FIG. 5E shows a further embodiment of a magnetic system in use. The operation is the same as described in FIG. 5A. In the embodiment shown in FIG. 5E, the teeth 204 are replaced with a ramp approach to move the lower magnet out of operable distance. By lifting the upper magnet, the lower magnet falls down onto a ramp 212 or sufficient angle to allow the lower magnet 207 to slide. Lower magnet 207 slides to a location out of communication. Upper magnet 209 is lowered to collect beads 210. Then magnetic head 104 is moved over the location containing lower magnet 207. Upper magnet 209 captures lower magnet 207, then head 104 is moved over the appropriate well. Magnet 209 is raised while maintaining operable communication with lower magnet 207 and beads 210 are released into the well.

Figure 6A:
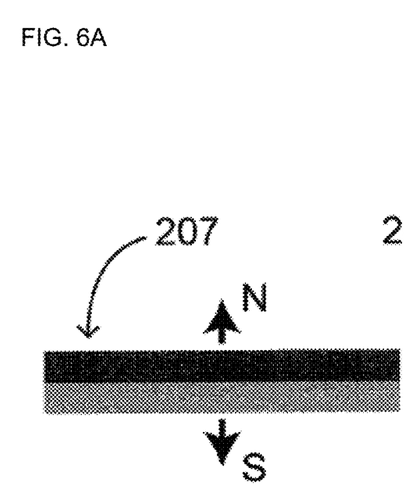
FIG. 6A shows a magnet in a configuration where the height of the magnet is less than the width.
Figure 6B:
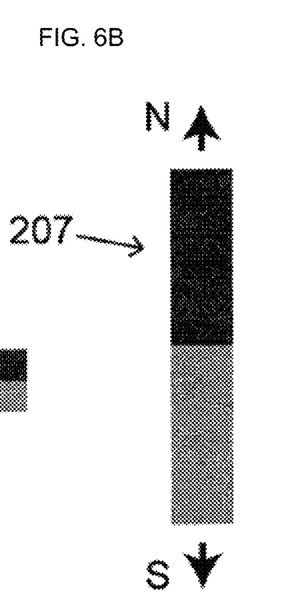
FIG. 6B shows a magnet in a configuration where the height of the magnet is greater than the width.

FIG. 6 shows exemplary magnet configurations. FIG. 6A shows an embodiment where the height of magnet 207 is less than the width. FIG. 6B shows an embodiment where magnet 207 in a configuration where the height of the magnet is greater than the width.

In some embodiments, the magnetic base does not contain or employ any electrical components (e.g. it is operated mechanically using only magnetic forces).

Sample processing system 100 may be used to process any type of liquid sample (e.g., biological sample) in order to isolate a variety of types of target analytes (e.g., proteins, nucleic acids, cells, etc.) from other components which may be present in liquid sample (e.g., solvent, blood, urine, sputum, plants, cells, etc.). As such, sample processing system 100 may be used as a platform for DNA or protein purification, cell separation, etc. Such techniques are widely used in basic laboratory research, drug discovery, disease diagnosis and monitoring, etc.

In some embodiments, the sample processing system is used to conduct or prepare sample for downstream analytical analysis. The present disclosure is not limited to particular analysis methods. Examples include, but are not limited to, sequencing analysis, hybridization analysis, and amplification analysis.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A magnetic box for a sample handling plate of a sample processing system, the magnetic box comprising:
    a) a top surface comprising a reagent plate mounting component;
    b) a bottom surface comprising a magnet management component comprising a plurality of sawtooth shaped ridges on the bottom of said top surface, wherein said top surface and said bottom surface partially define a magnet mounting cavity; and
    c) a lower magnet disposed in said magnet mounting cavity, wherein said sawtooth shaped ridges are configured to secure said lower magnet.

2. The magnetic box of claim 1, wherein said box further comprises a base and/or lid.

3. The magnetic box of claim 1, wherein said sawtooth shaped ridges have a depth of at least half a length or thickness of the lower magnet.

4. The magnetic box of claim 1, wherein said sawtooth shaped ridges are on a replaceable strip.

5. The magnetic box of claim 3, wherein said replaceable strip is integrated into a lid of said box comprising said top surface.

6. The magnetic box of claim 1, wherein said sawtooth shaped ridges comprise one or more ramped edges.

7. The magnetic box of claim 1, wherein said sawtooth shaped ridges comprise a pocket.

8. The magnetic box of claim 1, wherein said sawtooth shaped ridges comprise one or more square edges.

9. The magnetic box of claim 1, wherein said box further comprise a ramp on said bottom surface.

10. The magnetic box of claim 1, wherein the height of said lower magnet is less than or greater than the width of said lower magnet.

11. The magnetic box of claim 1, wherein said magnetic box comprises a material selected from the group consisting of a transparent plastic, a translucent plastic, ceramic, and a non metallic metal.

12. A system, comprising:
   a) the magnetic box of claim 1; and
   b) a magnetic head comprising an upper magnet.

13. The system of claim 12, wherein said system further comprises one or more additional components selected from the group consisting of a sample handling plate comprising a plurality of sample compartments, wherein said sample handling plate is in operable communication with said magnetic box, magnetic beads, a drive system configured to move said magnetic head, a sample handling plate cover configured to cover said sample handling plate, and a control component.

14. The system of claim 13, wherein said sawtooth shaped ridges are vertically or are not vertically oriented with sample compartments of said sample handling plate.

15. The system of claim 13, wherein said sample handling plate is a multi-well plate.

16. The system of claim 13, wherein said sample handling plate is not in fluid communication with said magnetic box.

17. The system of claim 13, wherein said upper magnet and said lower magnet are in magnetic communication with said sample handling plate.

18. A method of processing a sample, comprising:

a) contacting a sample and a plurality of magnetic particles with a first sample compartment a system, comprising i) a magnetic box comprising: a top surface comprising a reagent plate mounting component a bottom surface comprising a magnet management component comprising a plurality of sawtooth shaped ridges on the bottom of said top surface, wherein said sawtooth shaped ridges are configured to secure said lower magnet, and wherein said top surface and said bottom surface partially define a magnet mounting cavity; and a lower magnet disposed in said magnet mounting cavity; ii) a magnetic head comprising an upper magnet and iii) a sample handling plate comprising two or more sample compartments;

b) moving said upper magnet to a second sample compartment under conditions such that said lower magnet is vertically aligned with said upper magnet and wherein said magnetic management component secures said lower magnet in said second sample compartment;

c) returning said top magnet to said first sample compartment;

d) lowering said top magnet such that said magnetic particles are magnetically contacted with said top magnet; and e) moving said top magnet and said magnetic particles to said second sample compartment.

* * * * *